United States Patent [19]

Weil

[11] Patent Number: 5,047,166

[45] Date of Patent: Sep. 10, 1991

[54] SKIN TREATMENT COMPOSITION CONTAINING MONOESTER OF CITRIC ACID

[75] Inventor: Ira Weil, New York, N.Y.

[73] Assignee: Lever Brothers Company, Division of Conopco, Inc., New York, N.Y.

[21] Appl. No.: 376,451

[22] Filed: Jul. 7, 1989

Related U.S. Application Data

[62] Division of Ser. No. 24,233, Mar. 10, 1987.

[51] Int. Cl.$^5$ .................... C11D 9/06; C11D 15/04; C11D 1/08; C07C 69/74

[52] U.S. Cl. .......................... 252/132; 252/DIG. 16; 252/108; 252/117; 424/73; 514/547

[58] Field of Search ............... 252/132, DIG. 16, 117; 424/73; 514/547

[56] References Cited

U.S. PATENT DOCUMENTS

| | | | |
|---|---|---|---|
| 4,673,525 | 6/1987 | Small et al. | 252/132 |
| 4,695,395 | 9/1987 | Caswell et al. | 252/121 |
| 4,866,202 | 9/1989 | Weil | 560/180 |

FOREIGN PATENT DOCUMENTS 0199131  10/1986  European Pat. Off.

OTHER PUBLICATIONS

Antedating Prior Art with Constructive Reductions to Practice Under Rule 131. Part II: After In re Gosteli.
Antendating Prior Art with Constructive Reductions to Practice Under Rule 131. Part I; Before In re Gosteli.
In re Clark 148, USPQ 665 (CCPA 1966).
In re Spiller 182, USPQ 614 (CCPA 1974).
In re Stempel 113, USPQ 77 (CCPA 1957).
In re Stryker 168, USPQ 372 (CCPA 1971).
Chemical Abstract 93:31633h (1980) Stork, Karl.

Primary Examiner—Prince E. Willis
Assistant Examiner—J. Silbermann
Attorney, Agent, or Firm—James J. Farrell

[57] ABSTRACT

A skin treatment composition comprising a physiologically acceptable carrier and 1–35% by weight of a salt of a monoester of citric acid. The skin treatment composition imparts a pleasant smoothness to the skin and may be incorporated in several products to treat skin dryness. The hydrophobic group having an ester linkage to citric acid has 10 to 18 carbon atoms. Monoester of citric acid may be synthesized with low levels of di- and triester by forming citric acid anhydride and reacting this to form the monoester.

21 Claims, No Drawings

SKIN TREATMENT COMPOSITION CONTAINING MONOESTER OF CITRIC ACID

This is a divisional application of Ser. No. 024,233 filed Mar. 10, 1987.

The invention relates to compositions comprising effective amounts of a salt of a monoester of citric acid as skinsmoothing or softening agents. Additionally, an improved method of synthesizing monoesters of citric acid is claimed.

BACKGROUND OF THE INVENTION

Many compositions used for treating human skin impart unpleasant feel to the skin during or after use. Thus, many compositions containing soap, detergent or both and intended for cleansing the skin may dry the skin and leave it feeling rough, chapped and flaky. The drying effect of these compositions (which include toilet bars, liquid or powder hand washing and bubble bath compositions may be extremely pronounced in certain seasons, as in dry winter months. Use of such washing compositions during these seasons may dry the skin to the point of scaliness or brittleness, with resultant cracking, reddening, bleeding and soreness.

Other products applied to the skin such as shaving creams, foams or oils may also have a drying effect on skin. Moreover, the skin is stretched, scraped and often cut or punctured during shaving. These operations accompanying use of these products may exacerbate skin drying and increase skin feeling of roughness, flakiness and brittleness.

Products for the treatment of skin dryness include oils, balms, creams, lotions, liniments, ointments, unguents and gels. While these products may moisten skin and reduce or reverse roughness, cracking and brittleness of dry skin, many such products leave an unpleasant residue causing the skin to feel sticky, stiff, inflexible and waxy or unduly oily and greasy. Other products which may leave an unpleasant residue on the skin or which could benefit by improvement in skin treatment qualities include insect repellent and bite compositions, antiseptics and skin burn compositions (for burns from heat, sun or wind). Additionally, compositions for chapped lips such as lip balm or cream may impart an unpleasantly waxy or greasy feeling to the lips.

Citric acid derivatives have been incorporated in a wide variety of compositions. A salt of a monoester of citric acid, made from citric acid and alkanols of 1-18 or alkenols with up to 10 carbon atoms, is used to stabilize vinyl halide polymers in U.S. Pat. No. 3,362,923 (Kruth). Non-salt alkyl esters of citric acid in U.S. Pat. No. 3,929,712 (Hiyama et al.) are said to impart lubricant properties to vinyl chloride resins, each alkyl group having 12-22 carbons. Non-salt monoesters of citric acid are said to deactivate metals in petroleum products, e.g. cracked gasolines, according to U.S. Pat. No. 2,747,979 (Thompson). The radicals which esterify the citric acid may be alkyl or benzyl.

Monoesters of citric acid have also been used in treating clothes, as in U.S. Pat. No. 3,754,860 (Frick, Jr. et al.) where citrate monoesters with a small or moderate size aliphatic chain (up to 2-ethylhexyl) are included in wrinkle-resistant fabric finishes, and U.S. Pat. No. 3,971,626 (Heyden et al.) where a citric acid ester with a fatty alcohol of 12-22 carbon atoms is incorporated in a leather-treating agent. Particularly disclosed in Hayden et al. are citric acid esters with straight-chain unsaturated fatty alcohols and branched saturated or unsaturated fatty alcohols.

Monoesters of citric acid are also employed in the food technology art. U.S. Pat. No. 2,158,678 (Gooding et al.) describes agents said to retard the development of rancidity and improve moisture retention in glyceridic oil compositions, e.g., margarine. These agents, defined at col. 1, line 45 to col. 2, line 25, include monolauryl citrate and monostearyl citrate. Related U.S. Pat. No. 2,523,792 (Vahlteich et al.) describes edible compositions which are said to retard rancidity in glyceridic oils and which have 15 to 37.5% of selected monoesters of citric acid (including monolauryl, monomyristyl, monopalmityl, monooleyl and monostearyl citrate) dissolved in a solubilizing agent, e.g., lecithin. Monoesters of citric acid are also said to retard deterioration of milk and egg products in U.S. Pat. No. 2,667,419 (Gooding et al.). Citric acid monoesters of decanols, dodecanols, hexadecanols, and octadecanols are particularly disclosed and more particularly monolauryl and monostearyl citrate. Also, U.S. Pat. No. 2,902,372 (Harris) discloses monoesters of citric acid with aliphatic alcohols of less than 3 carbon atoms for the purpose of improving the whipping properties of egg whites. Finally, U.S. Pat. No. 3,004,853 (Julian et al.) discloses citric acid esterified with cetyl alcohol as part of an emulsifier system in a liquid shortening.

Other emulsifiers derived from citric acid, useful in the foods industry or cosmetology, are disclosed in U.S. Pat. No. 3,929,870 (David et al.). Specific citric acid derivatives in cosmetics include certain triesters of citric acid for shampoos disclosed in U.S. Pat. No. 4,176,176 (Cella) and 1-25% of citric or acetylcitric acid esterified by aliphatic alcohols having 1-6 carbon atoms for deodorant sticks and sprays disclosed in U.S. Pat. No. 4,010,253 (Reese et al.). European Patent 8105 (BASF) describes cosmetic preparations having 4-40% of citric acid esters carrying branched-chain alcohol radicals having 8-13 carbon atoms such as Tris-isodecyl citrate. German Patent No. 2,361,716 (Henkel) describes cosmetic preparations having 0.5-15% of coesters made from a) aliphatic diols, b) citric or acetylcitric acid, and c) aliphatic monofunctional alcohols having 12-30 carbon atoms. Preparations incorporating the coester are said to be soft and to produce no unpleasant feeling of sticking to the skin.

Citric acid or its derivatives have also been incorporated in toilet bars. Romanian Patent No. 72,330 (Grigorescu) describes incorporating citric acid in a cosmetic soap. U.S. Pat. No. 4,292,192 (Hooper) states that incorporating 0.3 to 3% of citric or acetylcitric acid esterified by an alkyl group of 1 to 4 carbon atoms imparts a deodorancy property to personal washing bars. (Another monoester incorporated in a personal washing composition, although not a citric acid derivative, is ROOC—$(CH_2)_n$—COOM, where R is an alkyl or alkenyl chain with 4-12 carbon atoms, n=2-4 and M is a cation disclosed in the currently pending U.S. Pat. application of Nambudiry et al., Ser. No. 914,022, filed Oct. 1, 1986 for Detergent Compositions.)

Citric acid derivatives have also appeared in detergent compositions as pollution control substitutes for other components. Thus, U.S. Pat. No. 3,816,318 (Hentschel) discloses washing, dishwashing and cleaning detergent compositions which include 5 to 30% of salts of certain monoesters derived from polybasic carboxylic acids and alcohols of at least 1 hydroxyl group and 1-8 carbon atoms. Hentschel states that owing to strengthened lipophilicity, the monoesters have heightened emulsifying properties. Specific monoester salts are disclosed.

U.S. Pat. No. 4,271,032 (Kolaian et al.) discloses compositions for removing soil from fabrics in laundering. The compositions include monoesters of certain polycarboxylic acids, the alcohol radical having 12-30 carbon atoms. The monoesters are said to be effective as a surfactant or as a builder. European Patent No. 199,131 (Raffineria Olii Lubrificanti), published Oct. 29, 1986, describes surfactants derived from citric acid, namely citric acid mono-, di- and triesters with alkoxylated alcohols described therein. Mixtures of these esters are said to be very efficient surfactants with excellent detergent and biodegradability properties and with little or no toxicity or skin irritancy. Mixtures of the esters are also said to be suitable for a liquid detergent for kitchenware as well as liquid or creamy skin detergents or bath foam, as set out in the Examples.

It has been discovered that salts of certain monoesters of citric acid impart desirable qualities to skin treatment compositions.

Some conventional methods of synthesizing monoesters of citric acid yield a mix of mono-, di-, and triesters of citric acid. The mixed mono-, di- and triester products of these methods is impractical in many applications. Only the monoester is soluble in alkaline aqueous systems. Additionally, the di- and triesters severely limit foaming. Thus, it would be desirable to produce monoesters of citric acid in a pure form, or in such predominance that the problems due to di- and triesters would be insignificant.

In the first of these methods, citric acid is reacted directly with an alcohol: the blend is heated, agitated until a solid forms, and cooled under reduced pressure, as described in U.S. Pat. Nos. 2,523,792 (Vahlteich) and 3,929,870 (David et al.).

A second method involves mixing citric acid in a dioxane solvent and adding an alcohol. The reaction mixture is refluxed for up to 72 hours, then the dioxane evaporated under reduced pressure. The remaining residue is diluted, then is stripped at 60° C. under reduced pressure. This method is described in U.S. Pat. No. 4,271,032 (Kolaian et al.). The yield of monoester of citric acid from both these direct esterification methods is about 60%. It is noted that dioxane is not only an expensive solvent; its use may be accompanied by peroxide compounds which, upon accumulation, may be explosive.

While the methods of synthesizing monoesters of citric acid produce a mixture of mono-, di- and triesters, the relative molar amounts of citric acid and alcohol affect whether the mono, di- or triester product predominates. Thus, reacting substantially equal molar amounts of citric acid and alcohol (or a greater amount of the former) favors monoester, while diester predominates when a molar amount of alcohol double that of citric acid is used.

One process which exploits this effect is described in U.S. Pat. No. 2,518,678. Citric acid is dissolved in dry pyridine. Stearyl alcohol is added to the solution and heated for 20 hours. Since only a small concentration of stearyl alcohol is said to be soluble in the pyridine solution, a small concentration of the alcohol is continually reacted with a large concentration of citric acid, favoring monoester formation.

However, even this process produces a mixture of mono-, di- and triesters, requiring expensive and cumbersome steps to purify the monoester such as the techniques of fractional crystallization and selective extraction with suitable solvent systems described in U.S. Pat. Nos. 2,518,678 and 2,523,792.

A. J. Repta et al., "Synthesis, Isolation, and Some Chemistry of Citric Acid Anhydride", Journal of Pharmaceutical Sciences 58, (Sept. 1969), pages 1110-1114, describes synthesis of citric acid anhydride at page 1, col. 2, lines 14-31 and page 2. Suggested uses of the anhydride are as a dessicant or an ingredient in formulations for carbonation.

In the Nambudiry application cited above, monoesters are prepared by mixing and heating an acid anhydride, e.g. succinic anhydride, with fatty alcohol.

It has been discovered that monoesters of citric acid may be produced with minimal levels of di- and triester if citric acid is first reacted to form citric acid anhydride then reacted to form the monoester.

SUMMARY OF THE INVENTION

This invention embraces a composition and a process. The process concerns synthesis of particular compounds, i.e., monoesters of citric acid, while the composition concerns salt forms of those compounds. Thus, while synthesis of, for example, the monoester of citric acid derived from triethoxylated dodecyl alcohol via the steps described below falls within the process of the invention, it is incorporation of a disalt such as disodium salt of the monoester into a physiologically acceptable carrier which comes within the composition part of the invention.

The composition aspect concerns a skin treatment composition comprising 1-35% of a salt of a monoester of citric acid and a physiologically acceptable carrier. It has been discovered that this composition has the desirable quality of imparting to skin a marked smooth and creamy feel. It has further been discovered that toilet bars incorporating a salt of a monoester of citric acid themselves have an unusually pleasant smoothness and slip.

The salt of the monoester of citric acid has one of the following formulae:

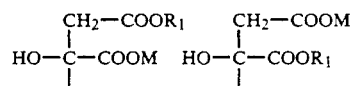

(I)          (II)

$R_1$ has the structure of a moiety derived from $R_1$-OH, which alcohol is selected from the group consisting of alcohols of the formula

or

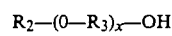

where $R_2$ is a hydrocarbon chain having 10 to 18 carbon atoms, A is an aryl group, $R_3$ is an alkyl chain having 2 to 4 carbon atoms and x is an integer from 1 to 7. Each M is a cation independently selected from the group consisting of alkali metals, alkaline earth metals, ammonium and substituted ammonium.

Skin treatment compositions incorporating 1-35% of a dication salt of a monoester of citric acid ester may be toilet bars, liquid hand washing compositions, shaving cream, antiseptics, insect repellent or bite compositions, and skin treatment compositions for dry, rough, or chapped skin or skin burned by heat, sun or wind.

The skin treatment composition of the instant invention may be in the form of a cream, liniment, oil, balm, ointment, solution, gel or unguent and may be applied directly to the skin. Incorporation of such compositions in pads, plasters, bandages, dressings, and pre-moistened towelettes, all optionally carrying medication in addition to the skin treatment composition, results in products embraced by this invention.

Without in any way limiting the scope of the present invention to the following theoretical considerations, applicant would like to emphasize his belief that it is the salt of the monoester of citric acid (rather than any di- or triester which may be present at very low levels) which contributes to the smoothening effect of the skin, and that maximizing the level of the monoester salt in skin treatment compositions results in markedly improved products. Moreover, it is important that the $R_1$ chain of the monoester be long enough to impart adequate hydrophobicity to the composition and to produce the smoothness and slip of such compositions. Consequently, it is monoesters having higher $R_1$ chain lengths which are included in the skin treatment compositions of the invention. These $R_1$ chains are typically straight chains, i.e., unbranched and not alkyl substituted.

The process aspect of this invention concerns synthesis of monoesters of citric acid. Pure or predominantly monoester is desirable for reasons stated above. It has been discovered that monoesters of citric acid may be synthesized with minimal production of di- or triesters: about 95% of the esterified citric acid is in monoester form, the balance being an acetyl derivative of the monoester. This new synthetic process produces higher yields in less time (75% and above in less than 12 hours) of a nearly pure monoester, and avoids the expense and difficulties associated with the solvent dioxane and purification of the monoester from the di- and triesters.

The process comprises heating citric acid with an organic anhydride to form citric acid anhydride. Then an alcohol of the formula $R_1$—OH is added to the reaction mixture, $R_1$—OH being defined as above. The reaction mixture is then continually distilled under reduced pressure to remove volatile materials such as liberated short chain acid side products. The monoester product may then be isolated as a dication salt and, if desired, isomers I and II may be purified. The isomer of formula (II) predominates in the product of this method by about a factor of 3, while the isomer of formula (I) predominates in the product of direct esterification by about a factor of 3.

DETAILED DESCRIPTION OF THE INVENTION

In its composition aspect, this invention relates to skin-smoothing compositions, which comprise, in admixture with a pharmaceutically acceptable carrier vehicle, an effective amount of a salt of a monoester of citric acid having one or both of the following formulae:

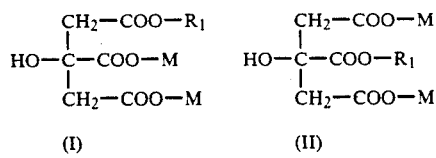

where $R_1$ is derived from $R_1$—OH, which alcohol is selected from the group consisting of alcohols of the formula

or

where $R_2$ is a hydrocarbon chain having 10 to 18 carbon atoms, A is an aryl group, $R_3$ is an alkyl chain having 2 to 4 carbon atoms, x is an integer from 1 to 7; and where M is a cation selected from the group consisting of alkali metals, alkaline earth metals, ammonium and substituted ammonium, particularly including mono-, di-, and trialkanol ammonium.

Compositions of this invention include a salt of an ester of citric acid. This ester of citric acid may consist essentially of the monoester of citric acid or may comprise a mixture of mono-, di- and triesters of citric acid.

The compounds of formulae (I) and (II) are isomeric forms of a salt of a monoester of citric acid, (II) being a symmetrical and (I) an asymmetrical isomer. Compositions of the present invention may have either isomer or a mixture of both. In a preferred embodiment, when both isomers are present, the relative amount of (II) to (I) may be about 3:1. Additionally, the monoester salts of citric acid need not all have identical $R_1$ groups. Furthermore, each molecule of the salt of a monoester of citric acid may have two of the same or different cations; if all the salt molecules have the same cations, the cations need not be the same from molecule to molecule.

$R_1$ may more particularly have the structure of a moiety derived from $R_1$—OH, which alcohol is selected from the group consisting of consisting of alcohols of formula (III) or (IV) with $R_2$ having 12 to 15 carbon atoms. Suitable mixtures of alkoxyl groups include the (3EO) ethoxylated primary alcohols with 12 to 15 or 14 to 15 carbon atoms, sold respectively as NEODOL 25-3 or 45-3. The NEODOL products are available ex Shell Oil Company, One Shell Plaza, Houston, TX 77002.

Instead of the 1 to 35% of a salt of a monoester of citric acid, the composition of the inventions may more particularly include from 5 to 30% or from 10 to 25% of the salt of a monoester of citric acid. At levels over 35%, compositions which are intended to be solid may become soft, mushy and pliable. (All component amounts expressed in percentages indicate percent weight unless otherwise stated.)

The compounds of formulae I and II may be incorporated in a physiologically acceptable carrier of petroleum jelly, lanolin, paraffin wax, alkanols, water and mixtures thereof as well as the carriers of the examples below. More particularly, the water may be a 1-5% solution of an appropriate buffer, such as sodium bicarbonate. The physiologically acceptable carrier may comprise soap or detergent toilet bars, or liquid or powder hand washing compositions, antiseptics, insect repellent and bite compositions, shaving creams, oils and foams, and compositions for treatment of dry, rough or chapped skin. Some formulations of the composition may be applied briefly and washed off, as in washing hands with a toilet bar within the invention, while other formulations such as a cream or ointment described below, may be left on indefinitely.

The skin treatment composition of the present invention may take any of the following forms: lotion, liniment, solution, suspensions, oil, ointment, cream, gel, balm, unguent, paste, stick or aerosol and may be applied directly to the skin. Application may also take place in using one of the consumer products listed above, e.g. in washing hands with a toilet soap bar. Alternatively, the skin treatment composition of this invention may be incorporated in pads or pre-moistened towelettes for a wiping application to the skin or onto bandages, dressings or plasters for a longer application. The bandages, dressings, pads, plasters and pre-moistened towelettes may be optionally medicated with substances in addition to the skin treatment composition.

Conventional soap compositions typically are comprised of from 25 to 90% by weight of soap and from 1 to 15% water. When such compositions further incorporate salt of monoester of citric acid within one of the above-recited ranges, the compositions come within the present invention. The term "soap" is used herein to mean the alkali metal or alkanol ammonium salts of aliphatic alkane or alkene monocarboxylic acids having about 12 to about 20 carbon atoms, and preferably about 12 to 18 carbon atoms.

It is preferred to use soaps having the fatty acid derived from coconut oil, tallow, or mixtures thereof, since these are among the most readily available fats. The proportion of fatty acids having at least 12 carbon atoms in coconut oil soap is about 85%. This proportion will be greater when mixtures of fatty acids derived from fats such as tallow, palm oil, or non-tropical nut oils or fats are used, wherein the principal chain lengths are of sixteen carbon atoms or more. The tropical nut oils include: palm kernel oil, babassu oil, ouricuri oil, tucum oil, cohune nut oil, murumuru oil, jaboty kernel oil, khakan kernel oil, dika nut oil, and ucuhuba butter. A preferred soap for use in the compositions of this invention has at least about 85% fatty acids having 12-18 carbon atoms.

Derivation of fatty acids from oils and fats for use in this invention is by known methods, e.g., saponification of said oil or fat.

An especially preferred soap composition comprises a mixture of alkali metal salts of fatty acids of which 10 to 70% are derived from coconut, and 90 to 30% are derived from tallow. More particularly, 15 to 20% of the fatty acids may be derived from coconut oil and 75 to 85% from tallow. These mixtures contain about 95% fatty acids having 12 to 18 carbon atoms.

Additionally, optional ingredients may be included in soap formulations of the present invention, e.g., free fatty acids, emollients, suds boosting agents, germicides, opacifiers (such as titanium dioxide) and colorants, pigments, perfumes, preservatives, electrolyte salts and mixtures thereof. A typical listing of the classes and species of optional ingredients useful in soap compositions appears in U.S. Pat. No. 4,260,507 incorporated herein by reference. It should be understood, of course, that these lists of optional ingredients and mixtures for soap compositions are only representative of such materials and is not intended to be limiting.

The soap compositions of the present invention may be in liquid or solid form. The latter form is well known commercially as the toilet bar. Requirements for a good toilet bar are well known and enumerated in U.S. Pat. No. 2,894,912. The properties of soap toilet bars of the present invention are similar to those of conventional bars with the addition of properties herein disclosed.

Soaps and Detergents, Thomssen and McCutcheon, MacNair-Dorland Co., 1949, pp. 195-207 and Kirk-Othmer Encyclopedia of Chemical Technology, John Wiley & Sons, 1983, Vol. 4, pp. 173-177 describe techniques of toilet bar-making including milling, plodding, framing and shaping, by means of which the soap compositions of this invention may be shaped into bars. A bar of toilet soap may be formed by these techniques from the following composition: about 80% of fatty acids derived from tallow and coconut, about 10% water and about 10% of disodium salt of a monoester of citric acid esterified with $C_{12}$-$C_{15}$ (3EO) primary alcohols. The bar itself has a remarkable smoothness and slip; washing with one's skin with the bar imparts a pleasant smoothness to the washed skin.

Non-soap skin-cleansing compositions may also come within this invention. These skin-washing compositions, with detergent active compounds replacing all or part of the soap in the toilet soap bars, are comprised of from about 10% to about 70% by weight of a detergent active compound, about 2% to about 20% suds booster, about 10% to about 40% by weight aliphatic fatty acid, about 2.5% to about 25% by weight water-soluble aliphatic fatty acid soap, about 1% to about 35% by weight of a salt or salts of monoester of citric acid and about 1% to about 10% by weight water. Additionally, the optional ingredients which may be included in these compositions are the same as those listed above for soaps.

Examples of detergent active compounds usable to form these compositions are found in "Surface Active Agents" by Schwartz & Perry (Interscience 1949) and "Surface Active Agents" by Schwartz, Perry & Berch (Interscience 1958) and those set forth in U.S. Pat. No. 2,894,912 and U.S. Pat. No. 3,070,547, each of which is hereby incorporated by reference. More particularly, the detergent active may be selected from the group consisting of alkali metal, magnesium or ammonium salts of detergents selected from the group consisting of $C_{12}$-$C_{16}$ hydroxyalkene sulfonates, $C_8$-$C_{18}$ N-acyl taurates, $C_{12}$-$C_{18}$ alkyl sulfates, $C_{12}$-$C_{18}$ alkyl ether sulfates, $C_{12}$-$C_{16}$ alkyl phosphonates and phosphates, $C_{12}$-$C_{16}$ mono-alkyl succinates and maleates, $C_6$-$C_{14}$ dialkylsulfosuccinates, $C_{16}$-$C_{20}$ alkane disulfonates, $C_8$-$C_{18}$ alkene sulfonates, alkylbenzene sulfonates and mixtures thereof. Further, The detergent active may be an alkali metal, magnesium or ammonium salt of a fatty acyl ester of isethionic acid, in particular fatty acyl esters derived from fatty acids having from 10 to 18 carbon atoms; more particularly the fatty acyl groups may be derived from fatty acids derived from coconut oil.

These skin cleansing compositions may be liquid or solid. The solid compositions may be formed into toilet bars according to the steps set forth in Thomssen and McCutcheon for soap bars. The properties of the detergent toilet bars of the present invention are similar to those of soap bars as well as to those of conventional bars with the addition of properties herein disclosed.

Skin-cleansing compositions of the present invention may incorporate soap or detergent active compounds or both. In addition to 10-35% of one of the soaps or detergent active compounds discussed above, or a mixture of both, a liquid hand cleansing composition of the present invention comprises 1 to 35% of a salt of a monoester of citric acid, 0-5% sodium chloride, and balance water. Optionally, this composition may further include 1-5% of a suds boosting agent, for example, coco monoethanolamide and 0.2-0.5% of a preservative, for example, EDTA.

When the composition of this invention is a toilet bar or liquid hand cleansing composition, it is desirable that little or no triester or salt of diester of citric acid be present, as these have been found to limit foaming and are insoluble in alkaline aqueous systems.

Shaving creams within the present invention comprise 1 to 35% of a salt of a monoester of citric acid, 25-50% stearic acid, 5-20% coconut oil, 10-25% glycerol, 1-15% mineral oil and 5-45% water.

A composition for treating dry, rough or chapped skin such as chapped lips under the present invention may be in solid form for use as a stick-type composition. Such compositions comprise from 1 to 35% of a salt of a monoester of citric acid, and from 50% to 98%, preferably 60% to 90%, of an emollient. This composition may further comprise from 1% to 20%, preferably 5% to 15%, of a suitable thickening agent, and optionally emulsifiers and water.

A typical listing of suitable thickening agents, emollients and emulsifiers useful in solid compositions appears in U.S. Pat. No. 4,560,549 (Ritchey et al.) incorporated herein by reference. It should be understood, of course, that the list of optional ingredients and mixtures there described is representative only and is not intended to be limiting. Additives commonly found in topical compositions such as preservatives, e.g. methyl and ethyl paraben, dyes and perfumes are advantageously included in any of the above-described solid compositions for treating dry, rough or chapped lips.

Compositions for treating dry, rough or chapped skin further may be in ointment form comprising 1 to 35% of a salt of a monoester of citric acid, 1 to 5% anhydrous wool fat, 5 to 20% viscous paraffin, 0 to 5% cetyl alcohol and 65-95% white petroleum jelly. More particularly, the cetyl alcohol may be present at 0.5-2.5%.

When the skin treatment composition of the present invention is in cream form, it comprises 1 to 35% of a salt of a monoester of citric acid, from 50 to 5%, preferably 25 to 10%, of an emollient, and the balance water. Optionally, the cream form contains a suitable emulsifier. The emollients and emulsifiers described above for compositions of the invention in stick form are equally suitable here.

The compositions of this invention may also be formulated in solution form, comprising from 1 to 35% of a salt of a monoester of citric acid, and 65 to 99% of a suitable organic solvent. Suitable organic materials useful as the solvent or a part of a solvent system are as follows propylene glycol, glycerine, ethanol, sorbitol esters, 1,2,6-hexanetriol, isopropanol, diethyl tartrate, butanediol, and mixtures thereof. Such solvent systems can also contain water.

The compositions of this invention may also be formulated in aerosol form by incorporating the solution formulation described above in a closed metal container fitted with an aerosol cap and pressurized using conventional methods at from 25 psi up to 100 psi pressure with an aerosol propellant such as butane gas.

In a gel form, the present invention comprises 1 to 35% of a salt of a monoester of citric acid, 5 to 75% and preferably 10-50% of an organic solvent, 0.5 to 20%, preferably 1 to 10% of a thickening agent, the balance being water. Suitable thickening agents include those recited above for compositions in solid form. Suitable organic solvents include but are not limited to glycerine, sorbitol esters, 1,2,6-hexanetriol, ethanol, isopropanol, diethyl tartrate, butanediol, and mixtures thereof.

The process aspect of this invention concerns synthesis of monoesters of citric acid. The process comprises mixing citric acid with an organic anhydride of the formula (IV):

(V)

where $R_4$ and $R_5$ are independently selected from the group consisting of hydrocarbon chains having from 1 to 5 carbon atoms or, with $R_4$ and $R_5$ taken together, containing 6 to 8 carbon atoms linked to form a cycloaliphatic or aromatic anhydride or substituted derivative thereof. More particularly, the anhydride may be acetic anhydride. The amount in moles of anhydride added is substantially equal to or slightly greater than the amount in moles of citric acid.

In a preferred embodiment, the citric acid and anhydride reaction mixture is heated to a temperature of from 60° C. to 90° C. for 15 to 45 minutes, producing citric acid anhydride, which is believed to have one of the following formulae:

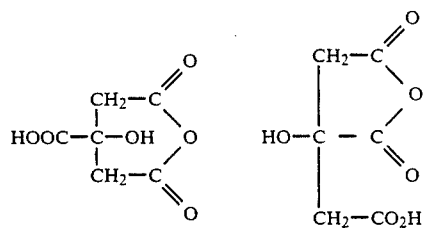

(VI)     (VII)

Regardless of the structure of any product or any intermediate in the reaction mixture at this stage, an alcohol of the formula $R_1$—OH may be added directly to the reaction mixture, $R_1$—OH being selected from the group previously defined. The amount in moles of alcohol added is substantially equal to or slightly less than the amount in moles of citric acid used to form the initial reaction mixture.

The citric acid anhydride and alcohol are subjected to heat and continuous distillation under reduced pressure to remove volatiles and produce predominantly the monoester of citric acid. In a preferred embodiment, the reaction mixture is heated to 60°-80° C. and continuously distilled at reduced pressure for 5-10 hours.

The monoester is in solution at this point. To isolate the monoester as a dication salt, the solution is cooled, diluted and neutralized with an organic or inorganic base. For example, the solution may be cooled to room temperature (25° C.) or below, diluted with a solvent such as ethanol or methanol, then neutralized to a pH of about 6.0 to about 8.5 with the solution at 15° C. or below. Organic or inorganic bases such as sodium hydroxide, potassium hydroxide, ammonia solutions, ammonium or substituted ammonium (particularly monoethanolamines), or salts thereof, alkali metal carbonates or alkaline earth metal carbonates or bicarbonates, or mixtures thereof may be used to neutralize the solution. The choice of the neutralizing reagent is governed by which salt or salts of the monoester of citric acid one wishes to form, since the cation of the neutralizing reagent becomes the cation of the monoester salt. The solid precipitate which forms is the salt of a monoester of citric acid of formula (I) or (II) above.

Alternatively, in another reaction mode, the citric acid may initially be placed in a solvent, such as acetone or an acid of the formula $R_6$—COOH, where $R_6$ is selected from the group consisting of hydrocarbon atoms having from 1 to 5 carbon atoms. An amount in moles of organic anhydride of the above formula (V) substantially equal to or slightly greater than the amount in moles of citric acid is added to the solution. The remainder of the steps are similar to those above.

Preferably, the citric acid used to form the monoester is anhydrous, to prevent lower yields due to hydrolysis of the anhydride reagent by water which may otherwise be present. Solvents employed for the citric acid preferably are also anhydrous.

It is an advantage of this process that predominantly monoesters are produced, i.e. about 95% of the esterified citric acid, the balance being an acetyl derivative of the monoester and minimal levels of di- and or triesters of citric acid. The synthesis of the present invention thus produces nearly pure monoester of citric acid.

Like the conventional direct esterification methods, the instant synthetic method yields a mixture of symmetrical and unsymmetrical isomers of citric acid monoester. However, the two methods yield relatively different isomeric products: the anhydride synthesis yields mainly symmetrical isomer predominating by about a factor of three over the unsymmetrical ester, while direct esterification yields mainly unsymmetrical ester predominating by roughly the same factor.

These isomers may be isolated from one another by known methods, among which are re-crystallization techniques. A preferred approach for isolating the symmetrical isomer of citric acid monoester from the unsymmetrical isomer follows: the monoester may be dissolved in a solvent system comprising 9 parts heptane and two parts ethyl ether. Adding an additional 1.5 parts ethyl ether induces precipitation. Once precipitation is complete, the solution may be filtered yielding pure symmetrical ester with melting point of 78-80.5° C.

In addition to the two isomeric forms of the monoester of citric acid, the citric acid anhydride process may form small amounts of diesters. However, the second ester linkage of this diester forms at the hydroxyl group of citric acid rather than at one of the carboxyl groups. The diesters apparently result from the reaction of the citric acid hydroxyl group with the short chain organic anhydride, the acid solvent, when used, or with the acid formed from hydrolysis of the anhydride. Thus, when acetic anhydride reactant for example is used to form citric acid anhydride, there may be formed some acetyl ester of citric anhydride. Subsequent reaction of the latter compound with long chain alcohols, for example, leads to formation of diesters. Such compounds usually comprise less than 10% of the citric acid monoester product and often comprise far less than 50%.

For a further understanding of this invention, reference may be made to the following examples:

EXAMPLE I

A toilet soap bar having the following composition is made by mixing the first three components in a Brabender kneader for 35 minutes at 50° C. then adding the last two components and mixing for 10 minutes more:

| | |
|---|---|
| Disodium salt of the reaction product of citric acid with primary alcohols having 12 to 15 carbon atoms and two ethylene oxide units | 17.6 |
| Mixture of sodium salts of fatty acids, of which 82% are derived from tallow and 18% are derived from coconut oil | 76.5% |
| Water | 3.8% |
| $TiO_2$ | 1% |
| Perfume | 1% |

EXAMPLE II

A toilet soap bar is made having the following composition by the steps of Example I:

| | |
|---|---|
| Disodium salt of the monoester of citric acid derived from dipropoxylated dodecyl-2-ene alcohol | 20% |
| Mixture of sodium salt of fatty acids of which 82% are derived from tallow and 18% from coconut oil | 70% |
| $TiO_2$ | 1% |
| Perfume | 1% |
| Water | balance |

The bars of Examples I and II impart a creaminess and smoothness to skin washed with the bars. Additionally, the bars themselves have a markedly pleasant smooth hand feel.

EXAMPLE III

A detergent toilet bar is made having the following composition: 10% of dipotassium salt of citric acid monoester derived from tetraethoxylated primary alcohols having 14 to 15 carbon atoms, 9% water, 50% of disodium salt of lauroyl ester of isethionic acid, 10% unesterified sodium salt of isethionic acid, 10% of potassium lauryl sulfate as a suds-boosting detergent salt, and 10% of paraffin wax as a binder-plasticizer. The toilet bar is formed by the conventional steps of toilet bar formation, and has the properties of the bars of Examples I and II.

EXAMPLE IV

A solid stick according to this invention containing a salt of a monoester of citric acid is prepared by shaping and molding the following ingredients:

| | |
|---|---|
| Disodium salt of the monoester of citric acid derived from diethoxylated decyl alcohol | 20% |
| Lanolin wax | 65% |
| Glycerol | 5% |
| Methylcellulose | 5% |
| Water | balance |

The resultant solid stick of this Example is applied upon the skin to relieve a feeling of dryness, roughness or scaliness.

EXAMPLE V

An ointment formulation is prepared by thorough mixing of the following ingredients.

| | |
|---|---|
| Dipotassium salt of a monoester of citric acid esterified saturated primary alcohols having 12 to 15 carbon atoms and three ethylene oxide units | 20% |
| Anhydrous wool fat | 2% |
| Viscous paraffin | 10% |
| White petroleum jelly | balance |

The resultant ointment is applied to the skin to relieve a feeling of dryness, roughness or scaliness. Advantageously, the ointment is applied every four to twelve hours while dryness persists.

EXAMPLE VI

A cream is prepared by mixing the following ingredients together:

| | |
|---|---|
| Disodium mono-n-tetradecylcitrate | 20% |
| Ethoxylated cholesterol | 20% |
| Sorbitol | 5% |
| Water | balance |

The resulting cream is applied to the skin to relieve dryness in the same manner as that described for the ointment in Example V.

EXAMPLE VII

A solution formulation is prepared by mixing the following components at room temperature:

| | |
|---|---|
| Glycerine | 60% |
| Disodium salt of the monoester of citric acid derived from triethoxylated lauryl alcohol | 15% |
| Water | balance |

The solution is applied to affected skin in substantially the same manner as that described for ointment in Example V.

EXAMPLE VIII

A gel formulation is prepared by mixing the following ingredients:

| | |
|---|---|
| Disodium salt of monoester of citric acid derived from tetraethoxylated saturated $C_{14}$-$C_{15}$ primary alcohols | 25% |
| 1,2,6-Hexanetriol | 45% |
| Bentonite | 8% |
| Water | balance |

EXAMPLE IX

Anhydrous citric acid (0.2 moles) and acetic anhydride (0.24 moles) rapidly mixed then heated to 70° C. for 20-30 minutes. Triethoxylated lauryl alcohol (0.18 moles) is added to the reaction mixture, which is then subjected to continuous distillation under reduced pressure at 70-75° C. for 5 hours to remove acetic acid.

The reaction mixture is cooled to 20° C. and diluted with ethanol, then neutralized at 15° C. to pH of 8.5.

Sodium carbonate (0.4 moles) is added and the disodium salt of the monoester of citric acid derived from triethoxylated lauryl alcohol is recovered as a precipitate.

EXAMPLE X

Anhydrous citric acid (0.2 moles) is placed in a vessel and suspended in acetic acid. Acetic acid anhydride (0.24 moles) is rapidly added to the vessel and the mixture is heated to 80° C. for 30 minutes. A mixture of dipropoxylated $C_{14}$-$C_{15}$ aliphatic alcohols is added to the vessel. The reaction mixture is continuously distilled at reduced pressure at 70° C. for 10 hours, then cooled to 25° C.

Ethanol (50 ml) is added to the vessel, then 50% aqueous NaOH is added to neutralize the mixture to about pH 7. The disodium salts of the monoesters of citric acid derived from dipropoxylated primary alcohols having 12 to 15 carbon atoms are recovered as precipitate.

In both of Examples IX and X yields of the disodium salt of monoester of citric acid are from 65% to 80%.

As will be readily apparent to persons of ordinary skill in the art to which the present invention pertains, various modifications of such invention as hereinbefore set forth and as further defined in the appended claims may be made without departing from the spirit and scope thereof regardless of the applicability of the theoretical bases advanced herein to elucidate of the invention.

What is claimed is:

1. A skin treatment composition comprising from about 1% to about 35% by weight of a dication salt of a monoester of citric acid having one of the following formulae:

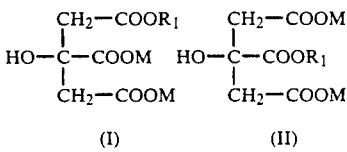

where $R_1$ has the structure of a moiety derived from $R_1$—OH, which alcohol is selected from the group consisting of alcohols of the formula:

$$R_2-A(O-R_3)_x-OH \qquad (III)$$

or $$R_2-(O-R_3)_x-OH \qquad (IV)$$

where $R_2$ is a hydrocarbon chain having 10 to 18 carbon atoms, A is an aryl group, $R_3$ is an alkyl chain having 2 to 4 carbon atoms and x is an integer from 1 to 7; each M is a cation selected from the group consisting of the alkali metals, the alkaline earth metals, ammonium, substituted ammonium and a mixture thereof; and a physiologically acceptable carrier for said monoester.

2. The skin treatment composition according to claim 1 wherein $R_1$—OH is selected from the group consisting of alcohols of the formula (III) or (IV) where $R_2$ is a hydrocarbon chain having 12 to 15 carbon atoms, $R_3$ is an alkyl chain of 2 carbon atoms and x is an integer of from 1 to 5.

3. The skin treatment composition according to claim 1 wherein $R_1$—OH is selected from the group consisting of alcohols of the formula (III) or (IV) where $R_2$ is a hydrocarbon chain having 14 to 15 carbon atoms, $R_3$ is an alkyl chain of 2 carbon atoms and x is an integer from 1 to 3, and 1 to 3 ethylene oxide units.

4. The skin treatment composition according to claim 1 wherein $R_1$—OH is selected from the group consisting of alcohols of formula (III) or (IV) where $R_2$ is a hydrocarbon chain having 12 to 15 carbon atoms, A is benzene, $R_3$ is an alkyl chain having 2 carbon atoms and x is an integer from 1 to 3.

5. The skin treatment composition according to claim 1 wherein the monoester of citric acid is comprised of symmetrical and unsymmetrical isomers in a relative ratio of about 3:1.

6. The skin treatment composition according to claim 1 wherein the skin treatment composition comprises a pharmaceutically acceptable carrier and from about 1 to 35% by weight of a salt of an ester of citric acid, the ester consisting essentially of the monoester of citric acid.

7. The skin treatment composition according to claim 1 comprising from about 5% to about 30% by weight of a salt of a monoester of citric acid, from about 25% to about 90% by weight of soap, and the balance water.

8. The soap composition according to claim 7 wherein fatty acids of the soap are derived from tallow.

9. The soap composition according to claim 7 wherein fatty acids of the soap are derived from a vegetable oil.

10. The soap composition according to claim 9 wherein the vegetable oil is coconut oil.

11. The soap composition according to claim 7 wherein fatty acids of the soap are derived from a mixture of tallow and coconut oil.

12. The soap composition according to claim 11 wherein 10 to 70% by weight of the fatty acids are derived from coconut oil and 90 to 30% by weight of the fatty acids are derived from tallow.

13. The soap composition according to claim 7 comprising about 10% disodium salt of the monoester of citric acid derived from triethoxylated lauryl alcohol, about 10% water and about 80% of a soap mixture comprised of from 75% to 85% of an alkali metal salt of fatty acids derived from tallow and from 15% to 25% of an alkali metal salt of fatty acids derived from coconut oil.

14. The soap composition according to claim 7 where the composition is formed into a toilet bar.

15. The skin treatment composition according to claim 1 comprising 30 to 70% by weight of a detergent active compound, 2 to 20% by weight of a suds booster, 10 to 40% by weight of an aliphatic fatty acid, 2.5 to 25% by weight of a water-soluble fatty acid soap, 1 to 35% by weight of a dication salt of a monoester of citric acid, and 1 to 10% by weight of water.

16. A skin treatment composition according to claim 15 where the composition is formed into a toilet bar.

17. The composition according to claim 15 wherein the detergent active compound is selected from the group consisting of alkali metal, magnesium or ammonium salts of $C_{12}$—$C_{16}$ hydroxyalkane sulfonates, $C_8$—$C_{18}$ N-acyl taurinates, $C_{12}$—$C_{18}$ alkyl sulfates, $C_{12}$—$C_{18}$ alkyl ether sulfates, $C_{12}$—$C_{16}$ alkyl phosphonates and phosphates, $C_{12}$—$C_{16}$ mono-alkyl succinates and maleates, $C_6$—$C_{14}$ dialkylsulfosuccinates, $C_{16}$—$C_{20}$ alkane disulfonates, $C_8$—$C_{18}$ alkene sulfonates, alkylbenzene sulfonates and mixtures thereof.

18. The composition according to claim 15 wherein the detergent active compounds are selected from the group consisting of alkali metal, magnesium or ammonium salts of fatty acyl esters of isethionic acid.

19. The composition according to claim 15 wherein the fatty acyl portions of the fatty acyl esters is derived from fatty acids having 10 to 18 carbon atoms.

20. The composition according to claim 19 wherein the fatty acyl portion of the fatty acyl esters is derived from fatty acids derived from coconut oil.

21. The skin treatment composition according to claim 1 comprising 10 to 35% by weight of a soap or a detergent compound or a mixture of both, 1 to 35% by weight of a dication salt of a monoester of citric acid, 1 to 5% by weight of a suds-boosting agent, 0.2 to 0.5% by weight of a preservative and the balance water.

* * * * *